United States Patent [19]

Umbeck

[11] Patent Number: 5,159,135
[45] Date of Patent: * Oct. 27, 1992

[54] GENETIC ENGINEERING OF COTTON PLANTS AND LINES

[75] Inventor: Paul F. Umbeck, Madison, Wis.

[73] Assignee: Agracetus, Middleton, Wis.

[*] Notice: The portion of the term of this patent subsequent to Apr. 2, 2008 has been disclaimed.

[21] Appl. No.: 575,035

[22] Filed: Aug. 30, 1990

Related U.S. Application Data

[63] Continuation of Ser. No. 937,384, Dec. 3, 1986, Pat. No. 5,004,863.

[51] Int. Cl.$^5$ .................... A01H 1/04; A01H 5/10; C12N 15/00; C12P 21/00
[52] U.S. Cl. ................................. 800/205; 800/255; 800/DIG. 27; 800/DIG. 63; 435/172.3; 435/69.1; 935/64; 935/67
[58] Field of Search ............... 800/205, 255, DIG. 27, 800/DIG. 63; 435/69.1, 172.3; 935/64, 67

[56] References Cited

U.S. PATENT DOCUMENTS

| | | | |
|---|---|---|---|
| 4,771,002 | 9/1988 | Gelvin | 435/172.3 |
| 4,940,835 | 7/1990 | Shah et al. | 435/172.3 |
| 5,004,863 | 4/1991 | Umbeck | 800/205 |

OTHER PUBLICATIONS

Zutra et al. 1982, Plant Disease 66(12): 1200–1201.
Widholm, J. 1988, TIBTECH 6: 265–266.
Rangan et al. 1984, In Vitro 20: 256.
Roy, et al., A sensitive and simple paper chromatographic procedure for detecting neomycin phosphotransferase II (NPTII) gene expression, *Plant Molecular Biology* 14: 873:876 (1990).
Zhou, et al., Introduction of Exogenous DNA into Cotton Embryos, *Methods in Enzymology*, vol. 101:433–481 (1983).
Bornman, C. H., "Alleviation of in vitro organogenic recalcitrance in sugar beet," In Vitro, vol. 21, No. 3, Part II (Mar. 1985).
Everett, N. P., et al. "Genetic Engineering of Inbred Lines of Sunflower," abstract, VI International Congress of Plant Tissue & Cell Culture (Aug. 1986).
Horsch, et al., "A Simple and General Method for Transferring Genes into Plants," *Science*, vol. 227, pp. 1229–1231 (Mar. 1985).
McCormick, et al., "Leaf disc transformation of cultivated tomato (*L. esculentum*) using *Agrobacterium tumefaciens*," *Plant Cell Reports* (1986) 5:81–84.
Schreier, et al., "The use of nuclear–encoded sequences to direct the light-regulated synthesis and transport of a foreign protein into plant chloroplasts," *The EMBO Journal*, vol. 4, No. 1, pp. 25–32 (1985).
Trolinder, et al., "Somatic embryogenesis and plant regeneration in cotton (*Gossypium hirsutum* L.)," *Plant Cell Reports* (1987) 6:231–234.
Trolinder, et al., "Somatic Embryogenesis in cell suspension cultures of *Gossypium hirsutum*," abstract, Proc. Beltwide Cotton Prod. Res. Conf. (1985).
Trolinder, et al., "Somatic Embryogenesis and Plant Regeneration in *Gossypium hirsutum* L.," *A Dissertation in Biology* (Dec. 1985).
Trulson, et al., "Transformation of cucumber (*Cucumis sativus* L.) plants with *Agrobacterium rhizogenes*," *Theor Appl Genet* (1986) 73:11–15.

*Primary Examiner*—David T. Fox
*Attorney, Agent, or Firm*—Quarles & Brady

[57] ABSTRACT

A method is disclosed to achieve genetic transformation of cotton plants and lines. Immature cotton tissues are genetically transformed in vitro, by Agrobacterium-mediated genetic transformation. The resultant cotton tissues are subjected to a selection agent or agents to screen for transformants. The transformed cultures are then induced to commence somatic embryogenesis. One possible regime for regenerating such somatic embryos into whole cotton plants is disclosed.

7 Claims, 1 Drawing Sheet

GENETIC ENGINEERING OF COTTON PLANTS AND LINES

This is a continuation of application Ser. No. 937,384, filed Dec. 3, 1986, now U.S. Pat. No. 5,004,863.

FIELD OF THE INVENTION

The present invention relates to the general technology of plant genetic engineering, and is related, in particular, to a strategy for the transformation and regeneration of cotton (*Gossypium hirsutum* L.) plants using the Agrobacterium method of plant genetic transformation so as to create novel genetically transformed cotton plants and lines.

BACKGROUND OF THE INVENTION

It is a general objective by many scientists working in the field of plant biotechnology to successfully genetically engineer plants of major crop varieties. While plant genetic engineering has been successfully demonstrated in several model plant species, often the model plant species, such as tobacco, carrot and petunia, are not the most economically important plant species for agricultural purposes. Accordingly, much effort has been directed toward the genetic engineering of the more agriculturally important plant species. By the term "genetic engineering" as used herein it is meant to describe the introduction of foreign, often chimeric, genes into one or more plant cells which can be regenerated into whole, sexually competent, viable plants which can be self-pollinated or cross-pollinated with other plants of the same species so that the foreign gene, carried in the germ line, can be inserted into or bred into agriculturally useful plant varieties.

The art of plant tissue culture has been an area of active research for many years but over the past five to ten years an intensified scientific effort has been made to develop regenerable plant tissue culture procedures for the important agricultural crops such as maize, wheat, rice, soybeans, and cotton.

Early publications on tissue culture of cotton dealt mainly with establishing the growing tissues from the plant under aseptic conditions in vitro. Davis, D. G. et al. In Vitro 9:395–398 (1974); Rani, A. and S. S. Bhojwani, *Plant Sci. Lett.* 7:163–169 (1976); and Price, H. J. et al., *Plant Sci. Lett.* 10:115–119 (1977). The methods detailed in these publications, however did not provide the necessary framework needed to regenerate cells back into while plants.

In the late 1970's, the development of somatic embryos, i.e., embryos derived from nongametic or somatic tissues, from the wild cotton species *G. klotzchianum* was reported. Price, H. J. and R. H. Smith, *Planta* 145:305–307 (1979). Unfortunately, there were two major problems those using the procedure of this report were unable to overcome. First, even after several more years of research, these investigators could not induce the somatic embryos to germinate, i.e., convert, to give rise to whole plants, Finer, J. J. and R. H. Smith, *Plant Cell Rep.* 3:41–43, 1984. Secondly, the same technique could not be successfully replicated using cultivated cotton as a plant tissue source.

Davidonis and Hamilton were the first to report successful regeneration of whole plants from somatic embryos of cotton. Davidonis, G. H. and R. H. Hamilton, *Plant Sci. Lett.* 32:89–93 (1984). These experimentors used immature cotyledon tissues of the cultivar Coker 310. The basic medium used consisted of Linsmaier and Skoog (LS) salts, vitamins, and the phytohormones NAA and kinetin. Linsmaier, E. M. and F. Skoog, *Physiol. Plant* 18:100–127 (1965). The tissues used in this report had been used in culture for several years without reports of similar results, and the exact procedures necessary to replicate this process are still not widely known.

During this same year, the regeneration of plants from several different California cotton cultivars was reported, with a protocol sufficiently developed that it could be replicated by the authors in reasonable time periods. Rangan, T. S. et al., In Vitro 20:256 (1984). In their procedure, several tissues, like cotyledons, immature embryos, and hypocotyl tissue, were cultured on Murashige and Skoog (MS) medium (Murashige, T. and F. Skoog, *Physiol. Plant.* 15:473–497, 1962) plus the phytohormones NAA and kinetin. After three-to-four months of culture, these tissues gave rise to embryogenic callus and somatic embryos. The embryos were then transferred to a low salt medium, e.g., Beasley and Ting's (BT) medium (Beasley, C. A. and I. P. Ting, *Amer. J. Bot.* 60:130–139, 1973) plus casein hydrolysate, which permitted some of them to germinate and grow into whole plants. About 200 plants were recovered using the Acala SJ-5 cultivar. Some sterility in the plants was observed and only 2% of the plants showed somaclonal variation.

Somatic embryogenesis was observed using the Coker line 312 and a Texas race stock called T25. Robacker, D. C. and T. W. Zimmerman, *In the Ann. Mtg. of the American Society of Agronomy*, November 25–30, Las Vegas, Nev. P. 85 (1984). The basal medium consisted of MS salts, the vitamins inositol and thiamine, sucrose, and the phytohormones NAA, 2,4 dichlorophenoxyacetic acid (2,4-D) and kinetin. Hypocotyls were used as the original tissue source. Even though embryos were recovered and cultured onto BT medium, no plants were recovered.

Other investigators have also reported somatic embryogenesis and plant regeneration. (Trolinder, N. L. and J. R. Goodin, *In the Proc. of the Beltwide Cotton Production Research Conferences*, Jan. 6–11, 1985, New Orleans, La. P. 46; and Mitten, D. H. *In the Proc. of the Beltwide Cotton Production Research Conferences*, Jan. 6–11, 1985, New Orleans, La. P. 57–58). These procedures were not published in detail, but based on the presentations, enough data was collected such that certain themes began to emerge. One investigator achieved somatic embryogenesis using the Coker 310 cultivar, immature embryos, and hypocotyl tissues on MS medium plus the phytohormones NAA and 2iP (or kinetin). While clear evidence was shown for somatic embryogenesis, the recovery of whole plants from these cultures was less clear. Other experimenters provided a clear and concise protocol. Repeatability was shown as was the recovery of intact plants. While they were able to obtain somatic embryos from several different lines, the best cultivars belonged to the Coker pedigreed lines 5110 and 312 and one Texas race stock, T25. Other cultivars were unable to complete the regeneration process, i.e. convert to whole plants, or were unable to form mature somatic embryos. Basically, their protocol used MS medium, B5 vitamins, and the phytohormones 2,4-D and kinetin.

These investigators have been focusing on plant regeneration of somatic non-transformed cotton tissues, but strategies directed toward the genetic engineering plant lines typically generally involve two complementary processes. The first process involves the genetic transformation of one or more plant cells of a specifically characterized type. By transformation it is meant that a foreign gene, typically a chimeric gene construct, is introduced into the genome of the individual plant cells, typically through the aid of a vector which has the ability to transfer the gene of interest into the genome of the plant cells in culture. The second process then involves the regeneration of the transformed plant cells into whole sexually competent plants. Neither the transformation nor regeneration process need be 100% successful, but must have a reasonable degree of reliability and reproducibility so that a reasonable percentage of the cells can be transformed and regenerated into whole plants.

The two processes, transformation and regeneration, must be complementary. It is possible to transform certain tissues or cell types which cannot be regenerated, and it is also possible to regenerate plant tissues of a number of different tissue and cell types which have not yet been successfully transformed, as demonstrated by the investigators discussed above. The complementarity of the two processes must be such that the tissues which are successfully genetically transformed by the transformation process must be of a type and character, and must be in sufficient health, competency and vitality, so that they can be successfully regenerated into whole plants.

Successful transformation and regeneration techniques have been demonstrated in the prior art for other plant species. For example, in Barton et al., "Regeneration of Intact Tobacco Plants Containing Full-Length Copies of Genetically Engineered T-DNA, and Transmission of DNA to R 1 Progeny", Cell 32:1033 (April 1983), the transformation and regeneration of tobacco plants was reported. Similar results have been achieved in some other plant species, though not cotton.

The most common methodology used for the transformation of cells of dicot plant species involves the use of the plant pathogen *Agrobacterium tumefaciens*. *A. tumefaciens* harbors a plasmid, referred to as the tumor-inducing or Ti plasmid, which has the natural ability to transfer a segment of itself, referred to as the T-DNA (transfer-DNA), into the genome of infected plant cells. Wild-type *A. tumefaciens* use this ability to genetically transform infected cells of plants so that the plant cells become tumorous, and also synthesize one of a series of compounds, known as opines, which can be metabolized by the infecting *A. tumefaciens*. It has been found by several investigators that by removing the bulk of the T-DNA from a Ti plasmid harbored by *A. tumefaciens*, and by replacing that T-DNA with a foreign gene construction, that the Agrobacterium can transform infected plant cells with the foreign gene in such a fashion that the resultant cells are not tumorous, as plant cells infected with wild-type normally *A. tumefaciens* are. The foreign gene construction is then included in the cells of a whole plant regenerated from the transformed cells and is then inherited in a simple Mendelian manner. The construction can thus be treated as any inheritable trait for crop breeding purposes.

Although the regeneration of whole plants from somatic embryos of cotton has been previously reported, it has not been heretofore thought to have been possible to genetically form whole cotton plants utilizing the transformation/regeneration techniques.

It is therefore an object of the present invention to genetically engineer whole intact cotton plants and lines.

It is further an object of the present invention to genetically engineer the production of whole cotton plants utilizing transformation/regeneration techniques.

It is still further an object of the present invention to genetically engineer the production of whole cotton plants, using the Agrobacterium method of gene transformation followed by a reproducible regeneration technique.

These objects and others are fulfilled by the present invention as described below.

SUMMARY OF THE INVENTION

The present invention involves the transformation of cotton cells in tissue culture and the regeneration of those cells into whole sexually mature cotton plants. It has been found that tissues derived from hypocotyl pieces of immature cotton plants can be inoculated with a culture of *A. tumefaciens* without adversely affecting the ability to elicit regenerable somatic embryo generation. Through the use of selectable markers, it is possible to screen, in the tissue culture stage, for transformed clonal growth of regenerable tissues to obtain whole plant development.

In brief, the process involves the steps of inoculating (or infecting) the hypocotyl pieces of immature cotton plants with an *A. tumifaciens* strain; tissue culture plating of the infected tissues; removing the bacteria from the infected tissues and simultaneously selecting tissues resistant to a selectable marker; amplifying the resistant tissues; and regenerating into whole plants.

The present invention is thus useful for the general genetic engineering of cotton plants and lines through the insertion into the germ line of such plants selected foreign genes.

DETAILED DESCRIPTION OF THE INVENTION

Figure 1:
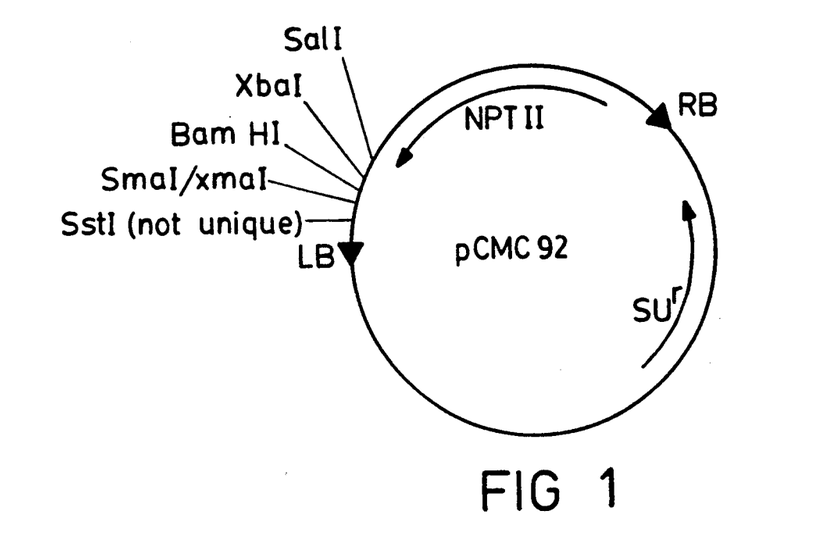
FIG. 1 is a schematic restriction enzyme mapping illustration of plant carrier plasmid pCMC92.
Figure 2:
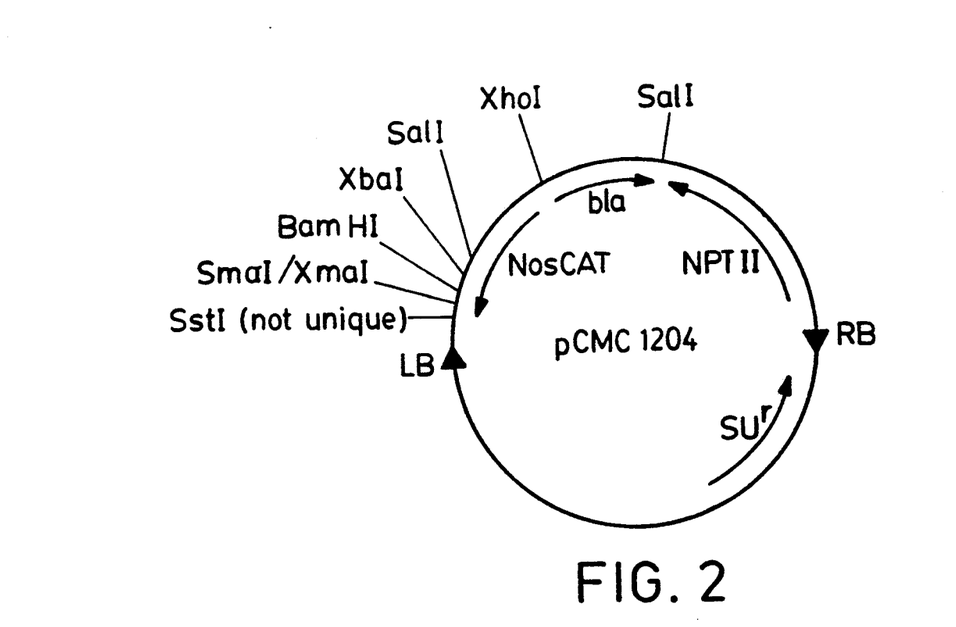
FIG. 2 is a restriction enzyme mapping illustration of the plant transformation plasmid pCMC1204.

The method of genetically engineering cotton plants and lines according to the present invention can, as stated above, be broadly thought of as involving two related processes. The first process is the genetic transformation of cotton cells or tissues in tissue culture. The second broad process is the regeneration of intact, sexually mature cotton plants from genetically transformed cells. The two processes are interdependent in that the tissues which are transformed in the regeneration process must be of a kind and of a competence so that they can be regenerated through the appropriate regeneration process. The present process envisions the genetic transformation of tissues in culture derived from hypocotyl explants excised from cotton plants four to six days after germination. The transformed tissues derived from the hypocotyl pieces can be induced to form embryonic structures, referred to here as somatic embryos, which can be regenerated into whole, relatively normal, and sexually competent cotton plants.

The transformation technique of the present invention is one which makes use of the Ti plasmid of *A. tumefaciens*. In using an *A. tumefaciens* culture as a transformation vehicle, it is most advantageous to use a non-oncogenic strain of the Agrobacterium as the vector carrier so that normal non-oncogenic differentiation of the transformed tissues is possible. It is also preferred, as a matter of convenience in preparing the actual genetic vector for transfer into the plant cells, that the Agrobacterium harbor a binary Ti plasmid system. In such a binary system, the Agrobacterium carries a first Ti plasmid having a virulence region therein and a second, chimeric plasmid, which contains therein the border regions of the T-DNA region of a wild-type Ti plasmid surrounding a chimeric gene construction including a foreign gene of interest. Binary Ti plasmid systems have been shown effective to transform plant cells. De Framond, *Biotechnology*, 1:262–269 (1983); Hoekema et al., *Nature*, 303:179 (1983). Such a binary system is preferred because the smaller plasmid, containing the T-DNA borders, can be constructed and manipulated most easily in an alternative host, such as *E. coli*, and then transferred into Agrobacterium. To be effective once introduced into cotton cells, the chimeric construction including foreign gene of interest must, in addition to a heterologous gene coding for a product of interest, contain a promoter which is effective in cotton cells to cause transcription of the gene of interest and a polyadenylation sequence or transcription control sequence also recognized in cotton cells. Promoters known to be effective in cotton cells include the "opaline synthase promoter, isolated from the T-DNA of Agrobacterium, and the cauliflower mozaic virus 35s promoter. It is also preferred that the binary plasmid harboring the foreign gene of interest also contained therein one or more selectable marker genes so that the transformed cells can be selected from non-transformed cells in culture. Preferred marker genes include antibiotic resistance genes so that the appropriate antibiotic can be used to segregate and select for transformed cells from among cells which are not transformed.

The heterologous gene selected for insertion into the cotton tissues can be any foreign gene selected to achieve a useful result if expressed in cotton plants. For example, expression of the *Bacillus thuringiensis* crystal protein toxin in the cells of cotton plants would make those cells toxic if ingested by Lepidoptera insects, thus inbuing the plants with a useful pest resistance. Expression of a viral coat protein in the cotton plant cells would make the plant resistant to infection by that virus. Transcription of negative strand RNA's in cotton plant cells can be useful for inhibition of undesirable endogenous genes or for disease resistance traits. As is understood by those skilled in the art, the demonstration here of the expression of a foreign protein in a cotton plant can readily be repeated with any other foreign gene of interest.

To commence a transformation process in accordance with the present invention, it is first necessary to construct the foreign genes of interest and properly introduce them into a transformation competent, but non-oncogenic, strain of *Agrobacterium tumefaciens*. The details of the construction of the vectors containing such foreign genes of interest are known to those skilled in the art of plant genetic engineering and do not differ in kind from those practices which have previously been demonstrated to be effective in tobacco, petunia, and other model plant species. The foreign gene should obviously be selected to accomplish some desirable effect in cotton plant cells. This effect may be growth promotion, disease resistance, a change in plant morphology or plant product (i.e. lint) quality, or any other change which can be accomplished by genetic manipulation. The chimeric gene construction can code for the expression of one or more exogenous proteins, or can cause the transcription of negative strand RNAs to control or inhibit either a disease process or an undesirable endogenous plant function.

To initiate the transformation and regeneration process for cotton plants, it is necessary to first surface sterilize cotton seeds to prevent inadvertent contamination of the resulting culture. The seeds are then allowed to germinate on an appropriate germinating medium containing a fungicide.

Four to six days after germination the hypocotyl portion of the immature plant is removed and sectioned into small segments averaging approximately 0.5 centimeters apiece. The hypocotyl explants are allowed to stabilize and remain viable in a liquid or agar plant tissue culture medium.

Once the hypocotyl segments have stabilized, they can promptly be inoculated with a suspension culture of transformation competent non-oncogenic Agrobacterium. The inoculation process is allowed to proceed for three to five days at room temperatures, i.e., 24° C.

At the end of the inoculation time period, it is necessary first to rinse off the excess Agrobacterium. Then the remaining treated tissues can be transferred to a second agar medium, which also contains one or more antibiotics toxic to Agrobacterium, but not to hypocotyl tissues, at a concentration sufficient to kill any Agrobacterium remaining in the culture. Suitable antibiotics for use in such a medium include carbenicillin and cefotaxime. The tissues are then given a period of from one to ten days to recover from the transformation process and are then continued in culture.

The tissues are now cultivated on a tissue culture medium which, in addition to its normal components, contains a selection agent, the selection agent being one toxic to non-transformed cotton cells but not to transformed cotton cells which have incorporated genetic resistance to the selection agent and are expressing that resistance. A suitable tissue culture medium is the MS medium to which is added the phytohormones 2,4 dichlorophenoxy-acetic acid (2-4,D), 6-furfurylaminopurine and a gelling agent. Suitable selection agents include both antibiotics and herbicides. Suitable antibiotic traits which may serve as dominant selectable markers include the aminoglycoside phosphotransferase-3'-II (APH-(3')-II) gene, also referred to as the neomycin phosphotransferase II gene (NPTII), which code for resistance to the antibiotic kanamycin, and the APH-(3')-IV gene which codes for resistance to Hygromycin B. Kanamycin, G418 and Hygromycin B are aminoglycosides that will step the growth of non-transformed cotton cells, but these antibiotics are phosphorylated by the appropriate enzyme if it is expressed in the transformed cells. Another suitable antibiotic selection agent is Chloramphenicol which can be acetylated and rendered non-toxic by the enzyme produced by the CAT (Chloramphenicol acetyl transferase) gene. Antibiotic dosed media allows only transformed cells to continue to grow and thrive. Thus the transformed cells, or calli, are allowed to grow on the selective medium. The surviving transformed tissues are transferred to a secondary medium to induce somatic embryogenesis. The surviving transformed tissue will thus continue to form into somatic embryos, which can then be regenerated through the regeneration technique of the present invention or through any other alternative plant regeneration protocols which use cotton somatic embryos as their starting point.

The selection process should continue for an extended time, i.e. 3-4 months, because of the slow growth of even transformed tissues on the antibiotic medium. Subcultures are made every 4-6 weeks to replenish nutrients and antibiotics. As the transformed cells are selected and amplified, individually derived cell lines are identifiable and can be removed and separately amplified.

The regeneration technique in accordance with the present invention begins with the tissues resulting from the transformation process. These tissues are putatively transformed calli which can generate somatic embryos when cultivated on appropriate embryo induction media. One technique for regenerating these somatic embryos to whole plants is disclosed here, but it is to be understood that other techniques are also possible, once transformed embryogenic tissues are produced.

The regeneration technique used by the applicants here thus begins with the tissues resulting from the transformation process. The cotton tissue calli, generated from the hypocotyl segments of the cotton plants, and putatively transformed, are placed onto somatic embryo induction media directly. At this point, the antibiotic selection agent should be removed from the culture medium, but otherwise the medium may remain constant. These calli, cultured on the somatic embryo induction medium, will form small embryoidal structures, which have been termed somatic embryos. It may take as long as two to three months for the somatic embryos to emerge and mature. Approximately 5 to as many as 20 somatic embryos will emerge from a single callus in an agar formulation of a somatic embryo induction medium. Many of the somatic embryos thus produced will be regenerable into whole plants in accordance with the technique described here.

When the developing somatic embryos are large enough, i.e. to a side of 4 mm or more in length, and if they appeared to have good embryonic development, i.e. usually having a cotyledon and a radicle, they may be transferred to large test tubes and hosted on fine vermiculite. The vermiculite is saturated with Stewart and Hsu (SH) medium (*Planta* 137:113 (1977)) plus the phytohormones indole acetic acid, 6-furfurylaminpurine and gibberellic acid. Small plantlets, having two to three leaves, eventually develop.

Once plantlet growth is established, i.e., the 2-3 leaf stage, the plants can now move into plant pots with vermiculite soil. They may be watered and fertilized as needed. They may also need to be hardened off, before greenhouse exposure. The plantlets may be repotted when they have 4-6 leaves after which they will continue to grow until mature.

The following examples will serve to illustrate the process of the invention without limiting the same.

EXAMPLE 1

Transformation of Callus

This example was designed to illustrate the transformation of cotton tissues in culture using virulent and avirulent strains of *A. tumefaciens* which carried plasmids that encoded for the marker enzymes neomycin phosphotransferase II (NPTII) (also known as APH-3'-II) and/or chloramphenicol acetyl transferase (CAT). The callus tissues were amplified over a period of several months on a selection medium. Tissue samples were removed and assayed for expression of the enzymes and the remaining tissues were used for DNA analysis. The details of the example are as follows:

Seeds of cultivated cotton (*Gossypium hirsutum* L.) of Coker lines 310, 312, 5110 Deltapine 61, and Stoneville 213 were surface sterilized with 3% sodium hypochlorite for twenty minutes. The seeds were then rinsed three times with sterile distilled water plus cefotaxime (500 mg/l). The seeds were allowed to germinate in SH medium containing the fungicide benomyl (50 mg/l). Four to six days after germination, hypocotyl explants were removed, cut into 0.5 cm pieces, and placed on a support medium containing agar (0.8%) and water.

The hypocotyl pieces were then inoculated with diluted (1:10) overnight culture of *A. tumefaciens*. The suspension culture of *A. tumefaciens* contained approximately $10^8$ bacteria per milliliter.

The particular *A. tumefaciens* strain used harbored a binary Ti plasmid system containing one Ti plasmid carrying the so-called virulence region and a second Ti plasmid containing T-DNA border regions from a virulent Ti plasmid (pCMC91, pCMC92 or pCMC1204) and also containing an antibiotic resistance gene (NPT II). One plasmid (pCMC1204) also carried a foreign gene (CAT) between the T-DNA borders. The infection of the *A. tumefaciens* on the immature embryonic tissues was allowed to proceed for three to five days at room temperature.

After incubation at room temperature and lighting, the tissues were transferred to Murashige and Skoog salts with B5 vitamins (Gamborg et al., *Exp. Cell Res.* 50:151-158 (1968)) plus antibiotics, the phytohormones 2,4-D (0.1 mg/l) and 6-furfurylaminopurine (0.1 mg/l), and the gelling agent Gelrite (1.6 g/l) (Gelrite is a registered trademark of Kelco Company, San Diego, Calif.) plus magnesium chloride (750 mg/l). The antibiotics used to kill the bacteria were cefotaxime (50-100 mg/l) and carbenicillin (400-500 mg/l). Kanamycin sulfate (5-50 mg/l) was included in the medium and used as a selective agent. Subcultures were made every four to six weeks to replenish depleted nutrients and antibiotics.

After three to four months, individually derived cell lines were labelled and maintained on a selection medium for tissue amplification. Tissues were incubated at 30° C. with a 16 hour photoperiod (50-100 umol/m²/s).

NPTII assays were carried out using crude cell extracts prepared from calli or plant tissues preincubated with a buffer solution (30 mM NaCl, 15 mM $NH_2Cl$, 3 mM MgCl, 5.5 mM Na EDTA, 2.3 mM Tris, 0.2 mM dithiothreitol (DTT), 105 mM sucrose at a pH of 7). Following three freeze-thaw cycles in liquid nitrogen, tissues were ground in buffer containing 37 mM Na EDTA, 126 mM NaCl, 83 mM $NH_2Cl$, 7.7 mM Tris, and 15 mM DTT. To protect against protease degradation of NPTII, 2.5 mM phenylmethylsulfonyl fluoride and 0.6 mg/ml leupeptin, 1.05 mg/ml soybean trypsin inhibitor and 5.0 mg/ml bovine serum albumin were added to the buffer. Forty microliters of extraction buffer was used per 100 mg (fresh weight) of callus or plant tissue. Supernatents were collected following centrifugation. Electrophoretic analysis of NPTII activity was carried out according to Paszknowski, J. et al., *EMBO. J.* 3:2717-2722 (1984); and Reiss, B. et al., 1984, *Gene*, 30:211-218 (1984).

Plant tissues were extracted according to the procedure of Herrera-Estrella et al., *Nature*, 303:209-213 (1983). The extracted plant tissues were CAT assayed as described by Gorman, C. M. et al., *Molec. Cell. Biol.* 2:1044-1051 (1982).

Table 1 lists the various vectors that were tested, the number of transformed lines obtained and the result of their NPTII test. Table 2 describes data collected for 5 samples of two of the vectors.

TABLE 1

Vector constructions that have been tested in cotton

| Vector | No. of Transformed Lines Recovered | No. of Lines Tested for NPTII | No. of Lines With (+) Assays | % |
|---|---|---|---|---|
| A6 | 4 | 4 | 0 | 0 |
| A6(pCMC91) | 21 | 21 | 16 | 76 |
| A6(pCMC92) | 16 | 16 | 16 | 100 |
| LBA4404 (pCMC91) | 17 | 17 | 15 | 88 |
| LBA4404 (pCMC92) | 4 | 4 | 4 | 100 |
| LBA4404 (pCMC1204) | 40 | 6 | 5 | 83 |

The A6 construction does not carry the Kanamycin resistance gene and, therefore, will not produce the NPTII protein. A6 is a virulent Agrobacterium strain. LBA4404 is a non-virulent strain. Plasmids pCMC91 and pCMC92 carry the NPT II gene alone between the T-DNA border segments. Plasmid pCMC1204 carries the NPT II and CAT genes in tandem.

TABLE 2

NPTII activity in transformed cotton callus

| Vector/Sample | cpm/20 ul crude extract | ng enzyme/20 ul* |
|---|---|---|
| Controls: | | |
| Stoneville 231 | 102 | L 0.1 |
| Coker 310 | 0 | L 0.1 |
| Deltapine 61 | 25 | L 0.1 |
| Vector LBA4404(92) | | |
| 1 | 26,320 | 3.06 |
| 2 | 77,016 | 8.97 |
| 3 | 31,190 | 3.63 |
| 4 | 53,413 | 6.20 |

Nanogram values were calculated from counts obtained from a known amount of NPTII enzyme run on the same gel. "L" indicates less than.

The results indicate the expression of at least one enzyme (NPTII) and/or in most cases the expression of both enzymes (NPTII and CAT) when they were incorporated together on the same plasmid in tissues of cotton callus in culture.

EXAMPLE 2

Transformation and Regeneration

In this example, cotton tissues were transformed using an avirulent strain of *A. tumefaciens* (LBA4404) which carried a plasmid (pCMC1204) that encoded for the marker enzyme NPTII and also for CAT. Over the next several months callus tissues were amplified on selection medium. Tissue samples were removed and assayed for expression of the enzymes. The remaining callus tissues were used to regenerate plants. Details of the example follow.

The plasmid pCMC1204 was constructed from components of a bipartite vector system similar to those previously described in the art. de Framond et al., *Bio/technology*, 1:262-269 (1983), Bevan, *Nuc. Acids Res*, 12:8711-8721 (1984). An expression cassette for the CAT gene was prepared by ligating the Hind III/Sau 3Al CAT coding fragment from pSV2CAT (Gorman et al. *Mol. Cell. Biol.* 2:1044-1051 (1982)) into the Hind III and Bam HI sites of pCMC66. The plasmid pCMC66 is an expression plasmid which employs the promoter and polyadenylation regions from the nopaline synthase nos gene of pTiT37 of Agrobacterium. The resulting CAT expression plasmid, designated pCMC1201, was linearized with Sal I which cuts the plasmid once immediately downstream of the polyadenylation region, and was inserted into the unique Sal I site on the carrier plasmid pCMC92. The carrier plasmid pCMC92 is a wide-host range replicon carrying the T-DNA border regions from Agrobacterium and a chimeric NPTII gene. The chimeric NPTII gene is formed from the nopaline synthase promoter and polydenylation sequence from pTiT37, i.e. the same control sequences as in pCMC66, and the NPTII coding region from Ti5. The product of the ligation was designated pCMC1204. Plasmid pCMC1204 was mobilized from *E.Coli* into *A. tumefaciens* strain LBA4404 in a triparental mating with a helper strain of *E.Coli* carrying pRK2013. Transconjugants were selected on plates containing streptomycin, sulfadiozone and carbenicillin at 100 microgram/ml. Single colonies were picked for amplification for inoculation of plant tissues.

The construction and use of both plasmids pCMC66 and pCMC92 is described in more detail in published patent application WO 85/04899 by Barton and Gelfand. The plasmid pCMC92 is on deposit with the ATCC, accession number 53093 and not only contains the chimeric NPTII gene and T-DNA borders, but contains the nopaline synthase promoter and polyadenylation sequences which can be removed from that plasmid and used with any desired heterologous coding sequence.

Hypocotyl pieces were inoculated with diluted (1:10) overnight cultures of *A. tumefaciens*. After three days incubation at room temperature (23°-27° C.) and lighting, the tissues were transferred to MS salts with B5 vitamins plus antibiotics, the phytohormones 2,4-D (0.1 mg/l) and 6 furfurylaminopurine (0.1 mg/l) and the gelling agent Gelrite (1.6 g/l), plus magnesium chloride (750 mg/l). The antibiotics used to kill the bacteria were cefotaxime (50–100 mg/l) and carbenicillin (400–500 mg/l). Kanamycin sulfate (5–50 mg/l) was included in the medium and used as a selective agent. Subcultures were made every four to six weeks to replenish depleted nutrients and antibiotics. After three to four months, individually derived cell lines were labeled and maintained on the selection medium for tissue amplification. The tissues were incubated at 30° C. for a 16 hour photoperiod (50–100 umol/m²/s).

After amplification, the antibiotics were discontinued and the transformed tissues were maintained on the same medium. After an additional 2 to 3 months, embryogenic calli emerged to give rise to somatic embryos. When the embryos were large enough, i.e., 4 mm or more in length, and appeared to have good embryo development, cotyledon and radicle present, they were transferred to large test tubes containing "fine" vermiculite. The vermiculite was saturated with SH medium plus the phytohormones indole acetic acid, 6 furfurylaminopurine and gibberellic acid, all at 0.1 mg/l. The embryos were incubated at a 30° C., 16 hour photoperiod. Upon germination, i.e., 2-3 leaf stage, plantlets were transferred to pots filled with vermiculite and watered and fertilized as needed. The plantlets were enclosed in a beaker for about one week to help hardenoff the leaves. Once potted-plantlet growth was established (4-6 leaf stage), they were moved to the greenhouse. Adapted plants were repotted in a commercial soil mixture, Metro Mix 360 (Metro Mix is a registered trademark of W. R. Grace and Co.), and maintained until mature.

The NPTII assays were performed according to the process outline in Example 1. The assays indicated NPTII activity in the leaf tissue of several of the regenerated cotton plants. Some plants grown from callus testing positive for NPTII activity tested negative, however.

To confirm the presence of the plasmid in the transformed plants, a Southern blot analysis was performed. The Southern blot analysis was performed with the restriction enzymes Ava I and Hind III, corresponding to the NPTII coding region. The plant DNA, extracted and digested, was hybridized with a radiolabeled negative strand NPTII sequence. A hybridizing band indicated presence of the expected fragment in the plant tissues in at least one copy number.

The plasmid pCMC 1204 was deposited with the American Type Culture Collection, 12301 Parklawn Drive, Rockville, Md., U.S.A., on Dec. 3, 1986 under ATCC accession No. 67275.

The above deposit was made pursuant to a contract between the ATCC and the Cetus Corporation, a partner in the assignee of the present invention. The contract with the ATCC provides for permanent availability of the progeny of these cell lines to the public on the issuance of the U.S. patent describing and identifying the deposit or the publication or laying open to the public of any U.S. or foreign patent application, whichever comes first, and for availability of the progeny of these cell lines to one determined by the U.S. Commissioner of Patents and Trademarks to be entitled thereto according to 35 USC Section 122 and the Commissioner's rules pursuant thereto (including 37 CFR Section 1.14 with particular reference to 886 O.G. 638). The assignee of the present application has agreed that if the cell lines on deposit should die or be lost or destroyed when cultivated under suitable conditions, they will be promptly replaced on notification with a viable culture of the same cell line.

The present invention is not to be limited in scope by the microorganisms deposited, since the deposited embodiment is intended as a single illustration of one aspect of the invention and any microorganisms which are functionally equivalent are within the scope of this invention. Indeed various modifications of the invention in addition to those shown and described herein will become apparent to those skilled in the art from the foregoing description and fall within the scope of the appended claims.

Although the present invention has been described with preferred embodiments, it is to be understood that modifications and variations may be resorted to, without departing from the spirit and scope of this invention, as those skilled in the art will readily understand.

I claim:

1. Cotton seed capable of germination into a cotton plant comprising in its genome a chimeric recombinant gene construction including a foreign gene and promoter and control sequences operable in cotton cells, the chimeric gene construction being effective in the cells of the cotton plant to express a cellular product coded by the foreign gene, the cellular product imbuing the plant with a detectable trait, the cellular product selected from the group consisting of a foreign protein and a negative strand RNA.

2. Cotton plants germinated from the seeds of claim 1.

3. Cotton seeds as claimed in claim 1 wherein the foreign gene codes for the production of a negative strand RNA effective to condition a somatic change to the cotton plant.

4. Cotton seeds as claimed in claim 1 wherein the promoter sequence is selected from the group consisting of the nopaline synthase promoter from *Agrobacterium tumefaciens* and the cauliflower mosaic virus 35s promoter.

5. A cotton plant comprising in the genome of at least some of its cells a foreign gene construction including promoter and control sequences effective in cotton cells, said gene construction further including a heterologous coding sequence, the foreign gene construction effective to cause expression of a detectable cellular product coded by the heterologous coding sequence in the plant cells, the cellular product selected from the group consisting of a foreign protein and a negative strand RNA.

6. A cotton plant comprising in its genome at least two foreign gene constructions each including promoter and control sequences effective in cotton cells, both gene constructions further including heterologous coding sequences, both foreign gene constructions effective to cause the expression of a detectable cellular product coded by the heterologous coding sequence in the plant cells, the cellular product of one of the foreign gene constructions selected from the group consisting of a foreign protein and a negative strand RNA, the other foreign gene construction being a selectable marker gene which imbues the cotton cells with the trait of resistance to a selection agent.

7. A cotton plant comprising in its genome at least two foreign gene constructions each including promoter and control sequences effective in cotton cells, both gene constructions further including heterologous coding sequences, both foreign gene constructions effective to cause the expression of a detectable cellular product coded by the heterologous coding sequence in the plant cells, the cellular product of one of the foreign gene constructions selected from the group consisting of a foreign protein and a negative strand RNA, the other foreign gene construction being a selectable marker gene which imbues the cotton cells with the trait of resistance to a selection agent, the foreign gene constructions having been transformed into the cotton plant or the progenitors of the cotton plant by Agrobacterium-mediated plant transformation.

* * * * *

US005159135B1

REEXAMINATION CERTIFICATE (4185th)

United States Patent [19]
Umbeck

[11] B1 5,159,135
[45] Certificate Issued Oct. 24, 2000

[54] GENETIC ENGINEERING OF COTTON PLANTS AND LINES

[75] Inventor: Paul F. Umbeck, Madison, Wis.

[73] Assignee: Agracetus, Inc., Middleton, Wis.

Reexamination Requests:
No. 90/003,297, Jan. 4, 1994
No. 90/003,453, Jun. 7, 1994

Reexamination Certificate for:
Patent No.: 5,159,135
Issued: Oct. 27, 1992
Appl. No.: 07/575,035
Filed: Aug. 30, 1990

Related U.S. Application Data

[63] Continuation of application No. 09/937,384, Dec. 3, 1986, Pat. No. 5,004,863.
[51] Int. Cl.$^7$ ............... A01H 1/04; A01H 5/00; A01H 5/10; C12N 15/82
[52] U.S. Cl. ............... 800/314; 800/278; 800/286; 800/294; 800/300; 800/288; 435/69.1; 435/468; 435/469
[58] Field of Search ............... 800/205, 255, 800/DIG. 27, DIG. 63, 278, 286, 288, 294, 300, 314; 435/69.1, 172.3, 468, 469; 935/64, 67

[56] References Cited

U.S. PATENT DOCUMENTS

| | | | |
|---|---|---|---|
| 4,672,035 | 6/1987 | Davidonis et al. | 435/240 |
| 4,940,835 | 7/1990 | Shah et al. | 800/205 |

FOREIGN PATENT DOCUMENTS 0 142 924   5/1985   European Pat. Off. .

OTHER PUBLICATIONS

Agrobacterium–Mediated Gene Transfer to Plants; Engineering Tolerance to Glyphosate, Horsch et al. Iowa State Journal of Research, vol. 62, No. 4, May 1988, pp. 487–502.

Transformed Callus Does Not Necessarily Regenerage Transformed Shoots, Jordan et al, Plant Cell Reports (1988), vol. 7; 285–287.

Growth and Survival of *Heliothis virescens* (Lepidoptera: Noctuidae) on Transgenic Cotton Containing a Truncated Form of the Delta Endotoxin Gene from *Bacillus thuringiensis*, Jenkins et al, Journal of Economic Entomology, vol. 88 (No. 1); pp. 181–185 (1993).

Prospects in Plant Genetic Engineering, Barton et al., Science, vol. 219, pp. 671–676 (1983).

A Vector for Introducing New Genes into Plants, Chilton, Scientific Am., Jun. 1983, vol. 248, pp. 51–59.

Use of a Chimeric Gene to Confer Antibiotic Resistance to Plant Cells, Fraley et al., Miami Winter Symposium, Advances in Gene Technology: Molecular Genetics of Plants and Animals, 1983, vol. 20 pp. 211–221.

Expression of bacterial genes in plant cells, Fraley et al., Proc. Natl. Acad. Sci, USA, vol. 80, pp. 4803–4807, Aug. 1983.

Ti Plasmids as Experimental Gene Vectors for Plants, Schell et al., 15th Miami Winter Symposium, Advances in Gene Technology: Molecular Genetics of Plants and Animals, 1983, vol. 20, pp. 191–209.

Advances in Gene Technology for Plants and Animals, Ledeboer and Malik, BioTechnology, Apr. 1983, pp. 169–171.

Inheritance of Functional Foreign Genes in Plants, Horsch et al., Science, vol. 223, pp. 496–498, Feb. 3, 1984.

(List continued on next page.)

*Primary Examiner*—David T. Fox

[57] ABSTRACT

A method is disclosed to achieve genetic transformation of cotton plants and lines. Immature cotton tissues are genetically transformed in vitro, by Agrobacterium-mediated genetic transformation. The resultant cotton tissues are subjected to a selection agent or agents to screen for transformants. The transformed cultures are then induced to commence somatic embryogenesis. One possible regime for regenerating such somatic embryos into whole cotton plants is disclosed.

OTHER PUBLICATIONS

The Use of the *Agrobacterium tumefaciens* Ti Plasmid As a Vector For the Genetic Engineering of Plant Cells, Hoekema et al., Innovations in Biotechnology, 1984, vol. 20, pp. 425–433.

Novel Approaches to Genetic Engineering in Plants, Zhou, G., Weng, J., Cell Biochem. (Suppl. 7B, p. 250) 1983.

Potential of Endophytic Bacteria For Biological Control of Fusarium Wilt of Cotton, Chen, C.Q. et al., Joint Meeting of the American Phytopathological Society and the Society of Nematologists on Plant Pathology Beyond 20000, Nashville, Tennessee, USA, Nov. 6–10, 1993, Phytopathology vol. 83(12), p. 1404, A647 (1993).

Gene Transfer to Plants: Assessment of Published Approaches and Results, Potrykus, I, Ann. Rev. Plant Physiol. Plant Mol. Biol. (1991), vol. 42, pp. 205,225.

Genetic Manipulation of Plants: from tools to agronomical applications, Steinbiss, H.H., and Davidson, A., Sci. Prog., Oxf. (1989) vol. 73, 147–168.

Gene Transfer Strategies in Plants, Sawahel et al., Biotech Adv., vol. 10, pp. 393–412, (1992).

Inheritance and Expression of Genes for Kanamycin and Chloramphenicol Resistance in Tansgenic Cotton Plants, Umbeck et al., Crop Science, vol. 29, No. 1 (1989), pp. 196–201.

Plant Regeneration from Callus Tissue of *Gossyplum hirsutum* L., Davidonis et al., Plant Science Letters, vol. 32 (1983), pp. 89–93.

Reynaerts et al 1988 Pl Molec Biol Manual A9: 1–3, 14–16.

Hinchee et al 1988 Bio/Technology 6:915–922.

Crossway et al 1986 (Feb.) Mol. Gen Genet 202:179–185.

Lapedes 1977 McGraw–Hill Encyclopedia of Food Agric & Nutrition, pp. 494–496.

The Language of Biotechnology 1988 ACS publisher, p. 217.

Glossary of Biotechnology Terms 1993 Technomic Publishing Co. pp. 26–27, 59, 121.

Dictionary of Microbiology and Molecular Biology, 1987, John Wiley & Sons p. 384.

A Dictionary of Genetic Engineering 1985, Cambridge Univ Press p. 44.

Roy et al 1990 Plant Molecular Biology 14: 873–876.

Hughes et al 1985 (Oct.) First International Congress of Plant Molecular Biology, Savannah GA, Abstract #P–01–184.

MiHen 1985 (Jan.) Proc. Beltwide Cotton Production Research Conference, New Orleans LA, pp. 57–58.

Phytogen News Release, Mar. 28, 1983.

Schell et al 1983 Bio/Technology (Apr. issue) pp. 175–180.

Caplan et al 1983 Science 222: 815–821.

Roy et al 1990 Plant Molecular Biology 14:873–876.

Finer et al 1983 TCA Report 17(5): 8,17.

Trolinder et al 1987 Plant Cell Reports 6: 231–234.

Trolinder 1985 (Dec.) Dissertation in Biology, Texas Tech Univ., Lubbock, TX.

Trolinder et al 1985 (Jan.) In Proceedings of Beltwide Cotton Production Research Conferences, New Orleans, LA, p. 46 (Abstract).

Zhou (1985) In Experimental manipulation of ovule tissues, Chapman et al (eds.), Longman, NY, pp. 240–250.

W. Jian et al., 1984, Acta Biochemica et Bipophysica Sinica, vol. 16, No. 3, pp. 325–327.

Agrios, *Bacterial Galls*, Plant Pathology, Academic Press, NY, 1978, pp. 483–488.

Barton, et al., *Regeneration of Intact Tobacco Plants Containing Full Length Copies of Genetically Engineered T–DNA, and Transmission of T–DNA to R1 Progeny Cell*, 32(4):1033–1043, Apr. 1983.

Butcher, et al., *The Role of Tissue Culture in the Study of Crown–Gall Tumorigenesis*, Tissue Culture Methods for Plant Pathologists, Ingram, et al. eds. (1980).

Zhou, et al., *Introduction of Exogenous DNA into Cotton Embroys*, Methods in Enzymology, 10:433–481 (1983).

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-7 is confirmed.

* * * * *